(12) United States Patent
Farley et al.

(10) Patent No.: US 6,214,010 B1
(45) Date of Patent: Apr. 10, 2001

(54) RONGEUR SURGICAL INSTRUMENT

(75) Inventors: Daniel K. Farley, Traverse City; Anthony J. Mulac, East Jordan, both of MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 0 days.

(21) Appl. No.: 09/433,894

(22) Filed: Nov. 4, 1999

(51) Int. Cl.[7] .................................................. A61B 17/00
(52) U.S. Cl. ................................................................ 606/83
(58) Field of Search ............................ 606/83, 170, 171, 606/209

(56) References Cited

U.S. PATENT DOCUMENTS

| | | | |
|---|---|---|---|
| 1,040,523 | * | 10/1912 | Vilbiss ..................................... 606/83 |
| 2,790,437 | * | 4/1957 | Moore ..................................... 606/170 |
| 4,586,497 | * | 5/1986 | Dapra et al. ............................ 606/80 |
| 4,733,663 | | 3/1988 | Farley . |
| 4,777,948 | * | 10/1988 | Wright ..................................... 606/83 |
| 5,009,661 | * | 4/1991 | Michelson ............................. 606/170 |
| 5,269,797 | * | 12/1993 | Bonati et al. .......................... 606/170 |
| 5,273,519 | | 12/1993 | Koros et al. . |
| 5,312,407 | | 5/1994 | Carter . |
| 5,451,227 | | 9/1995 | Michaelson . |
| 5,484,441 | | 1/1996 | Koros et al. . |
| 5,562,699 | * | 10/1996 | Heimberger et al. ................. 606/170 |
| 5,569,258 | | 10/1996 | Gambale . |
| 5,681,337 | | 10/1997 | Bray, Jr. . |
| 5,782,834 | | 7/1998 | Lucey et al. . |
| 5,873,873 | | 2/1999 | Smith et al. . |

* cited by examiner

Primary Examiner—Gene Mancene
Assistant Examiner—Eduardo C. Robert
(74) Attorney, Agent, or Firm—McAndrews, Held & Malloy, Ltd.

(57) ABSTRACT

A rongeur has a frame and a reciprocating member slidably associated with the frame. A blade is disposed on the distal end of the reciprocating member. The frame has a handle that is coupled with the reciprocating member for slideable movement of the reciprocating member. In this fashion, the blade is moved into a cutting position against a footplate formed in the distal end of the frame. A flexure is associated with the handle which allows the handle to be flexed. To reduce the potential for breakage of the footplate, a stop mechanism is provided for preventing further movement of the reciprocating member when the flexure is flexed.

22 Claims, 3 Drawing Sheets

RONGEUR SURGICAL INSTRUMENT

BACKGROUND OF THE INVENTION

Field of the Invention

The present invention relates to a surgical instrument, and more particularly to an improved rongeur surgical instrument having a mechanism to reduce the likelihood for breakage of the footplate and/or cutting mechanism thereof.

In surgical procedures, it is important to optimize treatment of the patient yet minimize the potential for breakage of the surgical instrument. One instrument used in certain surgical procedures is an instrument called a rongeur. A rongeur is a type of heavy-duty forceps for removing small pieces of bone, cartilage, or other tissue from the human body. Rongeurs are used, for example, in medical procedures performed on vertebrae of the back (i.e., laminectomy rongeurs). Laminectomy rongeurs are specifically designed to remove the lamina of the spine. The lamina is a bony plate that protects and covers the spinal cord.

A rongeur typically includes a frame comprising a barrel supported at a proximal end by a pistal-shaped grip. A footplate or cutting anvil is mounted at the distal end of a shaft disposed within the barrel. In at least one embodiment, the barrel, having a cutting blade at its distal end, is positioned for reciprocating axial movement from a first position to a second position (wherein the cutting blade is in contact with the footplate). The reciprocating movement of the cutting blade is provided by squeezing a trigger mechanism, such as a pull handle that is pivotally mounted to the frame of the rongeur. Small segments of bone or tissue may be removed by placing the same in an aperture formed in the barrel between the cutting blade and the footplate and then squeezing the trigger.

The underside of the lamina is in very close proximity to the spinal cord and nerve roots. It will therefore be understood by those skilled in the art that the footplate of the rongeur must be very thin so that can it fit between the patient's lamina and nerve structure. It will also be understood by those skilled in the art that, because the footplate is thin, it is susceptible to breakage when excess pressure is transferred from the trigger mechanism to the cutting blade. This may occur, for example, when the subject portion of a bone that is encountered is of a hardness or thickness that may not be cut by the rongeur without breakage of the footplate. Breakage of the footplate is therefore a matter of serious concern for the surgeon.

Accordingly, it is an object of the present invention to reduce the potential for breakage of the footplate.

It is a further object of the present invention to reduce the transfer of excess force to the footplate.

BRIEF SUMMARY OF THE INVENTION

These and other objects of the present invention are accomplished by an improved rongeur having a frame and a reciprocating member slidably associated with the frame. A handle is coupled with the reciprocating member for slidable movement of the reciprocating member. A flexure that is movable between a flexed position and an unflexed position is associated with the handle. A stop mechanism is provided for preventing movement of the reciprocating member when the flexure is flexed.

Other objects and advantages of the invention will become apparent upon reading the following description and upon reference to the drawings.

DETAILED DESCRIPTION OF THE INVENTION

Figure 1:
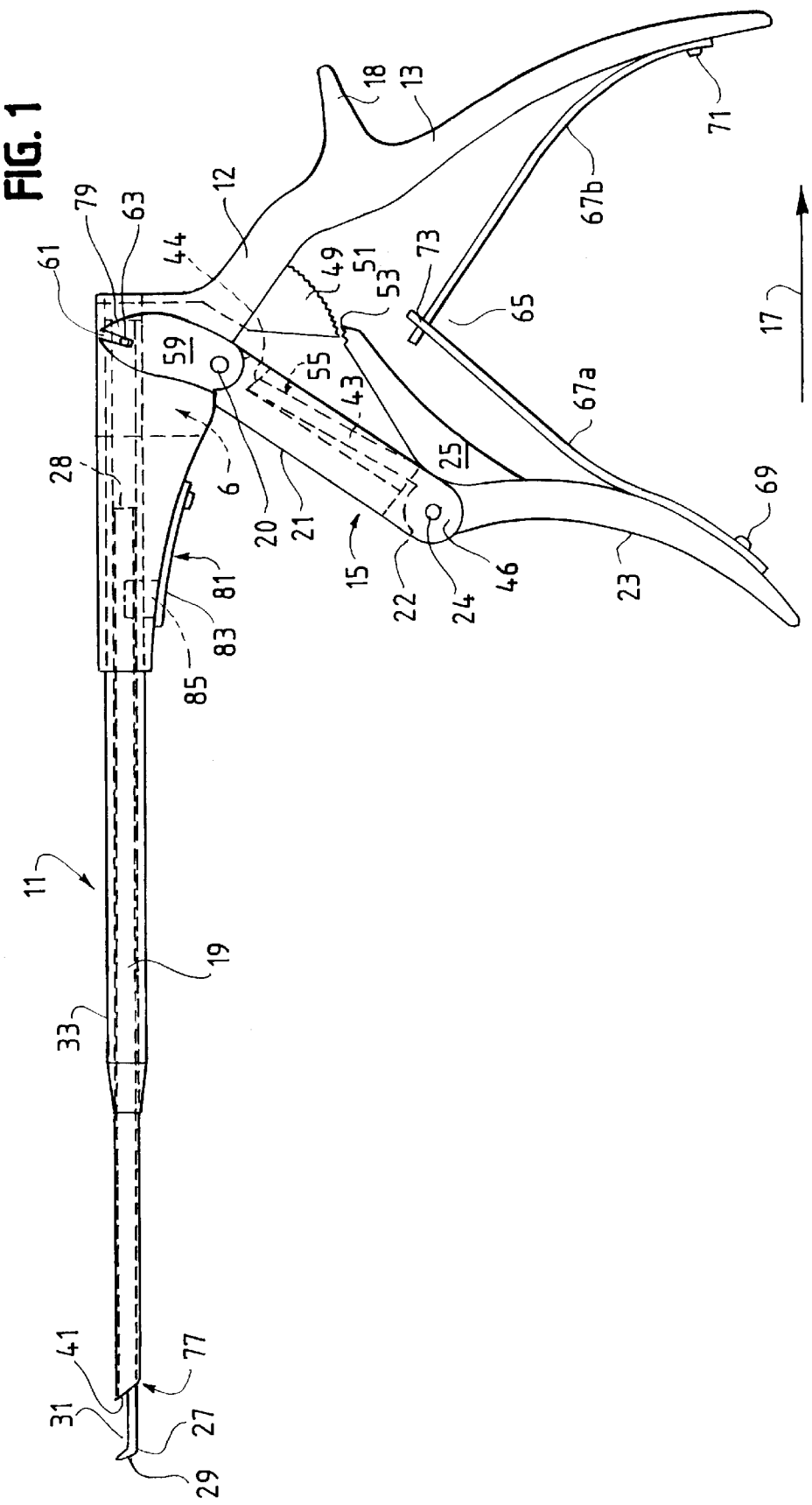
FIG. 1 is a plan view of a rongeur of the present invention in partial cross-section.

Turning first to FIG. 1, there is shown a rongeur 11 comprising a frame 12 and having a stationary handle 13 and a pull handle 15 arranged to be held within the human hand in which the pull handle may be rotatably moved in the direction of arrow 17. The stationary handle 13 is fixed relative to the frame 12 and is preferably integrally associated with the frame 12. The rongeur 11 is preferably made from stainless steel for ease of sterilization, although it could be constructed of other materials.

As shown, the stationary handle 13 is curved to form essentially a pistol grip. A nub 18 is formed in the stationary handle 13 and extends outwardly to engage the user's hand just above the thumb and forefinger. The pull handle 15 comprises an arm 21 that is pivotally associated with the frame 12 at axis 20 and a flex handle 23 that is pivotally associated with the arm 21 at axis 24. The arm 21 has an arm head 59 that is sized to fit within a pocket 6 formed in the frame 12. The arm head 59 has a slot 61 formed therein to accommodate a pin 63 for coupling the arm 21 with a barrel 33 (discussed below). The flex handle 23 is preferably crescent shaped and of a length sufficient to comfortably accommodate the user's forefingers.

A return spring 65 is associated with the stationary handle 13 and the pull handle 15. The return spring 65 generates a returning force to return the pull handle 15 to its starting position as shown in FIG. 1. The return spring 65 is formed of spring steel made of two distinct and separate spring members 67a and 67b (FIG. 1). One of each of the spring members 67 is rigidly attached to the flex handle 23 and the stationary handle 13, respectively, at lower extremity points 69 and 71, while being hingedly interlocked at an intermediate contacting point 73. Alternative spring mechanisms could be used, such as a single spring member having two ends, one of which is attached to the flex handle 23 (or pull handle 15) and the other to the stationary handle 13, or a spring mechanism whereby one end is not fixedly attached to either handle.

The frame 12 has a shaft 19 that is preferably removably attached thereto by a latch 81. The latch 81 is comprised of a relatively flat spring 83 having a tab 85 projecting upwardly therefrom. The tab 85 is sized and configured to mate with a notch (not shown) on the shaft 19, thereby fixedly attaching the shaft 19 to the frame 12. In this manner, the shaft 19 may be easily removed from the frame 12 (for ease of cleaning or disassembly) by pulling downwardly on the flat spring 83. Alternatively, the shaft 19 may be attached to the frame 12 by a screw, welding, or the like.

The shaft 19 has a distal end 27 and a proximal end 28. Although it may be shaped in a variety of ways, the shaft 19 is preferably formed of a cylindrical or oval shaped bar having a uniform cross-section that is sized to accommodate axial movement of the barrel 33 about the outer circumferential surface of the shaft 19 (discussed below). A footplate 29 is formed from the distal end 27 of the shaft 19 in a generally upward direction. An aperture 31 is formed in the distal end of the shaft 19 adjacent to the footplate 29. The aperture 31 provides an opening or work area of sufficient size and shape to accommodate bone or other matter to be cut in the manner discussed below.

The barrel 33 is elongated and has an inner cross-sectional shape that is configured to slide over the shaft 19. The barrel 33 has a distal end 77 and a proximal end 79. A slot (not shown), which extends from its proximal end 79, is formed along the bottom of the barrel 33. The slot is sized and positioned to accommodate the tab 85 of the latch 81, thereby allowing the barrel 33 to slide axially over the shaft 19 without interference from the tab 85. The pin 63 (referenced above) is disposed normal to the axis of the barrel 33 near the proximal end 79 of the barrel 33. The pin 63 is sized and positioned to pivotally engage the slot 61 formed in the arm head 59.

The pocket 6 (referenced above) is sized and shaped to accommodate movement of the arm head 59 as the pull handle 15 is moved in the direction of arrow 17. A blade 41 for cutting bone or other matter is mounted on the distal end 77 of the barrel 33. The blade 41 is sized and positioned so that is can move freely over the shaft 19. The barrel 33 is of a sufficient length such that the blade 41 may selectively protrude towards, and contact, the footplate 29 at the distal end 27 of the shaft 19. In this fashion, the barrel 33 transfers force from the arm 21 to the blade 41 for cutting bone at the location of the aperture 31.

Figure 4:
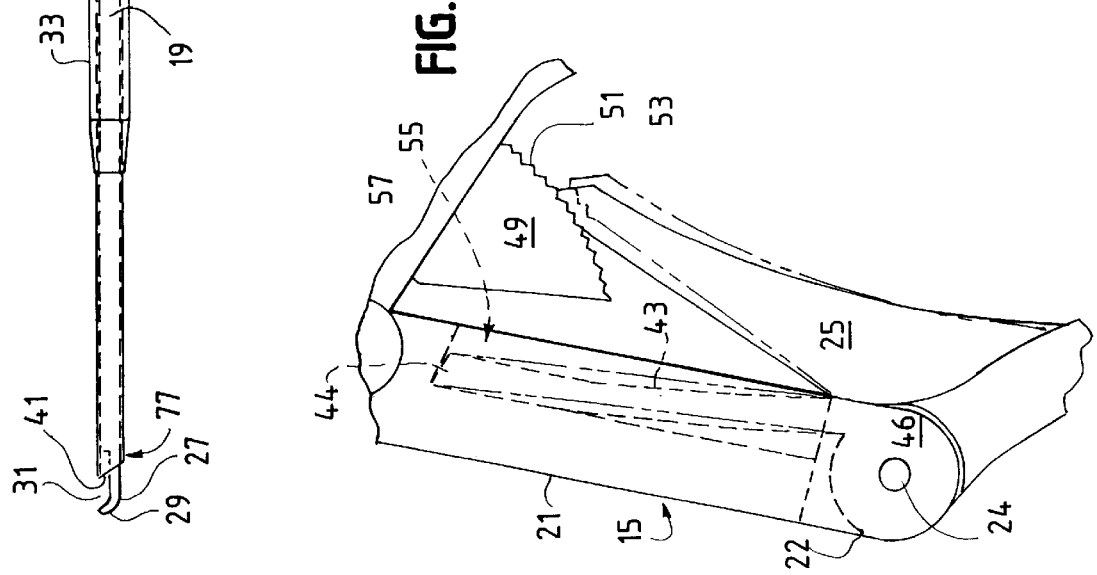
FIG. 4 is a partial view of the rongeur of FIG. 3.

A flexure 43 is pivotally associated with the distal end 22 of the arm 21 at second axis 24, extending inwardly towards the frame 12. The flexure 43 may be shaped in the form of a finger and is preferably formed from hardened stainless steel so as to better impart a spring-like quality. The flexure 43 has a base 46 which is affixed to the proximal end of the flex handle 23. The flexure 43 therefore pivots along axis 24 upon flexing of the flex handle 23. As best shown in FIG. 4, the arm 21 preferably has a channel 55 formed therein that is sized and shaped to accommodate limited movement of the flexure 43. Preferably, the flexure 43 is configured so that it will not freely move out of the channel 55 (FIG. 4). In this respect, the distal end 44 of the flexure 43 is angularly shaped and abuts the top surface 57 of the channel 55 which prevents the flex handle 23 from freely rotating out of the channel 55 (FIG. 4).

A stop base 49 is connected to the frame 12 and is disposed between the arm 21 and the handle 13. Alternatively, the stop base 49 may be connected to the handle 13 or other suitable location so as to accomplish its function as disclosed herein. The stop base 49 preferably extends in a radial downward fashion from the frame 12 and terminates in a distal end upon which teeth 51 are formed. A stop member 25 is connected to and projects rearwardly from the flex handle 23. The stop member 25 is positioned so as to engage the stop base 49 when the flex handle 23 is in its flexed position (as discussed below). The stop member 25 preferably has teeth 53 disposed at its distal end. The teeth 53 are sized and positioned to engage the teeth 51 of the stop base 49 upon flexing of the flex handle 23.

Figure 2:
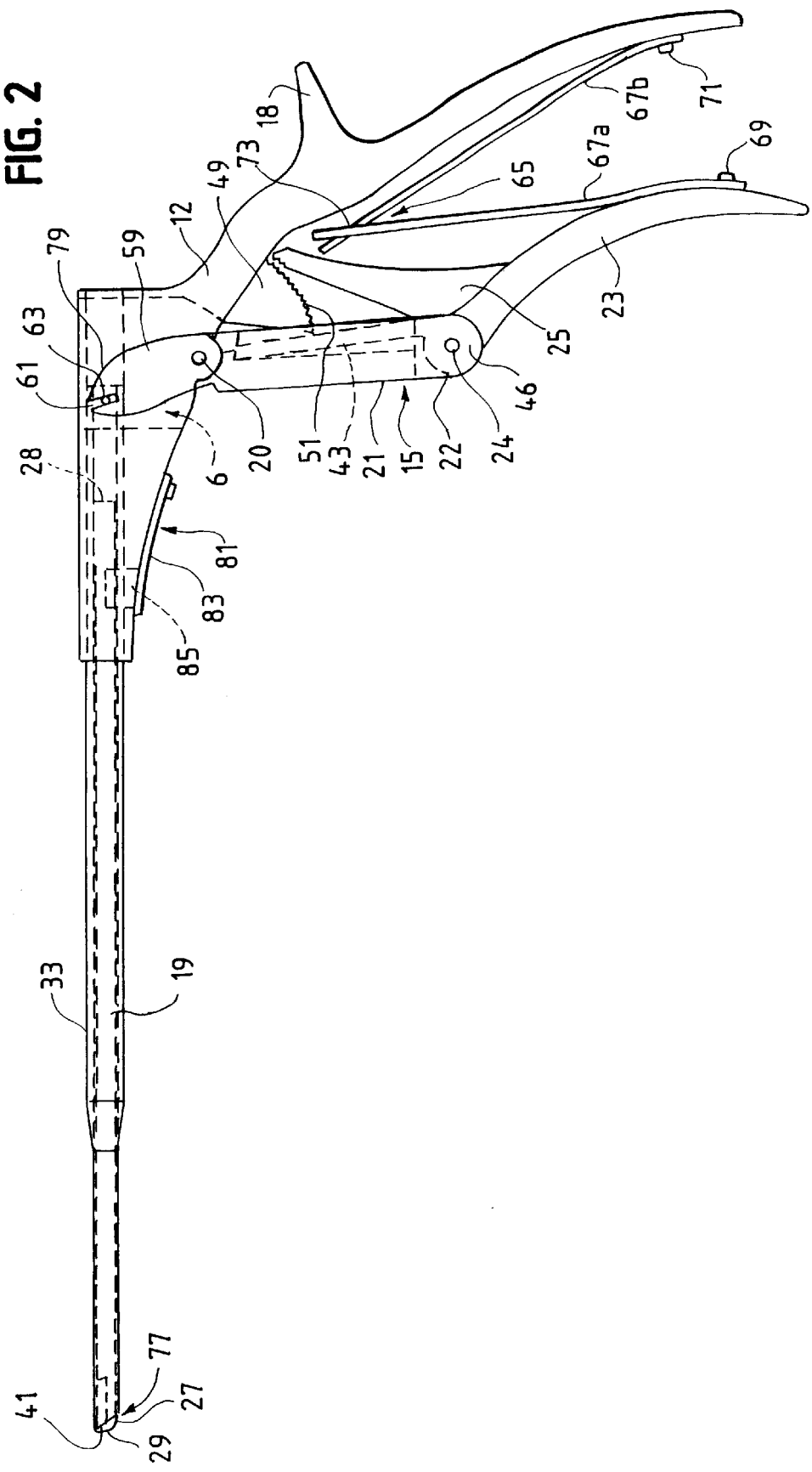
FIG. 2 is a plan view of the rongeur of FIG. 1 showing the pull handle in a closed and unflexed position.

When a squeezing force is applied to the flex handle 23 in the direction of arrow 17, the barrel 33 is moved axially towards the distal end of the shaft 19. This causes the blade 41 to move into contact with the footplate 27. As shown in FIG. 2, when the flex handle 23 is in an unflexed position, the teeth 53 of the stop member 25 do not engage the teeth 51 of stop base 49. In such case, the pull handle 15 may move freely along axis 20.

Figure 3:
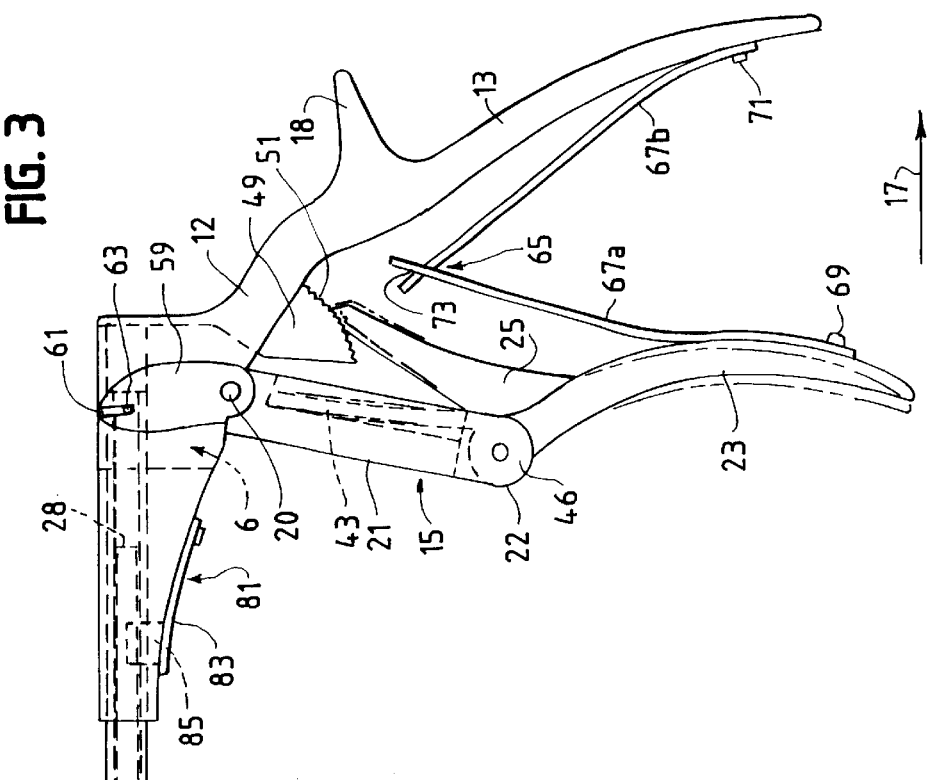
FIG. 3 is a plan view of the rongeur of FIG. 1 showing the pull handle in a flexed position.

As shown in FIGS. 3 and 4, when a piece of bone to be cut is too thick or hard for the blade 41 to cut without applying such force that would risk damage to the footplate 29, the flex handle 23, and thus also the flexure 43, both move pivotally about axis 24. The flexure 43 engages the interior surface of the channel 55 of the pull arm 21. (The phantom lines show the flex handle 23 and flexure 43 in their unflexed positions.) In such case, the teeth 53 of stop member 25 engage the corresponding teeth 51 of the stop base 49, thereby providing a stop mechanism for preventing further movement of the pull handle 15 in the direction of arrow 17. This also prevents further movement of the barrel 33 and hence also prevents further pressure against the footplate 29 by the blade 41. As a result, the potential for breakage of the blade 41 and the footplate 29 is significantly reduced. Upon release of pressure on the flex handle 23 by the surgeon, the return spring 65 causes the pull handle 15 to return to its open position. The surgeon may then select a smaller bite of bone to be cut and proceed without risking damage to the footplate 29 and blade 41 of the rongeur.

While we have shown a presently preferred embodiment of the present invention, it will be apparent to those skilled in the art that the invention may be otherwise embodied within the scope of the appended claims. By way of example and not limitation, the rongeur may comprise two moveable handles. By way of further example, the disclosed stationary handle 13 may alternatively be a push handle, and the flexure 43 and/or stop member 25 can be associated with the push handle.

What is claimed is:

1. A surgical instrument comprising:
   a frame,
   a reciprocating member slidably associated with said frame;
   a handle coupled with said reciprocating member for slidable movement of the reciprocating member;
   a flexure associated with said reciprocating member, the flexure movable between an unflexed position and a flexed position; and
   a stop mechanism actuatable by the flexure when in its flexed position.

2. The surgical instrument of claim 1 wherein said stop mechanism comprises a stop base and a stop member, whereby said stop member and stop base are positioned for engagement when the flexure is in its flexed position.

3. The surgical instrument of claim 2 wherein the stop base has a distal end extending radially outwardly from said frame and having a plurality of teeth formed therein, said teeth positioned to engage the stop member when the flexure is in its flexed position.

4. The surgical instrument of claim 3 wherein the stop member has a distal end having one or more second teeth formed therein, said second teeth sized and positioned to engage the teeth of said stop base when the handle is moved from its first position towards its second position.

5. The surgical instrument of claim 4 wherein the handle comprises a flex handle and an arm, said arm pivotally associated with said frame, and said flex handle pivotally associated with the arm from a first position to a second position.

6. The surgical instrument of claim 1 wherein the handle comprises a flex handle and an arm, said flex handle pivotally associated with the arm between a first position to a second position.

7. The surgical instrument of claim 6 wherein said flexure is pivotally associated with said flex handle.

8. The surgical instrument of claim 7 wherein the arm has a channel formed therein, said channel sized and positioned to accommodate limited movement of said flexure.

9. The surgical instrument of claim 8 wherein the stop mechanism comprises a stop base and a stop member, whereby said stop member and stop base are positioned for engagement when the handle is moved from its first position towards its second position.

10. The surgical instrument of claim 9 wherein the stop base has a distal end extending radially outwardly from said frame and having a plurality of teeth formed therein, said teeth positioned to engage the stop member when the handle is moved from its first position towards its second position.

11. The surgical instrument of claim 10 wherein the stop member extends from said flex handle and has a distal end having one or more second teeth formed therein, said second teeth sized and positioned to engage the teeth of said stop base when the flex handle is moved from its first position towards its second position.

12. The surgical instrument of claim 1 wherein the flexure comprises a base connected to the handle and finger portion extending therefrom.

13. A surgical instrument comprising:
a frame;
a barrel slidably associated with said frame between a first position and a second position;
a handle associated with said barrel for providing reciprocal movement of said barrel between its first and second positions;
a means for flexing said handle between a first position and a flexed position; and
a means for preventing further movement of said barrel towards its second position when said handle is in its flexed position.

14. The surgical instrument of claim 13 wherein said barrel has a distal end and comprising in addition a cutting blade disposed on the distal end of barrel; a shaft disposed at least partially within said barrel, said shaft having a distal end and a proximal end; an aperture formed in the distal end of said shaft for inserting material to be cut; wherein said aperture is sized to slide within the distal end of said barrel when said barrel is in its second position.

15. The surgical instrument of claim 13 comprising in addition a shaft, wherein the barrel has an inner circumferential surface that is sized to slide over said shaft.

16. The surgical instrument of claim 13 wherein the means for flexing said handle comprises a flexure.

17. The surgical instrument of claim 16 wherein the flexure comprises a base connected to the handle and finger portion extending therefrom.

18. The surgical instrument of claim 16 wherein the handle comprises an arm and in addition a flex handle pivotally associated with said arm.

19. The surgical instrument of claim 18 wherein the means for flexing said flex handle comprises in addition a channel formed in said arm, said channel sized and positioned to accommodate limited movement of said flexure.

20. The surgical instrument of claim 19 wherein the means for preventing further movement of said barrel comprises a stop member and a stop base and said stop base has a distal end having a plurality of teeth framed therein.

21. The surgical instrument of claim 20 wherein the stop base has a distal end extending radially outwardly from said frame and having a plurality of teeth formed therein, said teeth positioned to engage the stop member when the handle is in a flexed position.

22. The surgical instrument of claim 21 wherein the stop member has a distal end having one or more second teeth formed therein, said second teeth sized and positioned to engage the teeth of said stop base when the flexure is in its flexed position.

* * * * *